United States Patent [19]

Nishimuta et al.

[11] Patent Number: 4,685,951
[45] Date of Patent: Aug. 11, 1987

[54] TOBACCO AXILLARY BUD REGULATING COMPOSITION

[75] Inventors: Kouichi Nishimuta, Saitama; Kazuo Izumi; Kazue Shinsugi, both of Hyogo, all of Japan

[73] Assignee: Sumitomo Chemical Company, Ltd., Osaka, Japan

[21] Appl. No.: 813,524

[22] Filed: Dec. 26, 1985

[30] Foreign Application Priority Data

Jan. 4, 1985 [JP] Japan ................................ 60-278

[51] Int. Cl.$^4$ .................................... A01N 43/56
[52] U.S. Cl. ............................. 71/78; 71/92
[58] Field of Search ........................ 71/78, 92

[56] References Cited

U.S. PATENT DOCUMENTS 3,852,056 12/1974 Draber et al. ............................ 71/78
3,888,654 6/1975 Abramitis ................................ 71/78
4,124,369 11/1978 Kramer et al. .......................... 71/78

FOREIGN PATENT DOCUMENTS 0076030 4/1983 European Pat. Off. ............... 71/92

*Primary Examiner*—Glennon H. Hollrah
*Assistant Examiner*—Amelia A. Owens
*Attorney, Agent, or Firm*—Cushman, Darby & Cushman

[57] ABSTRACT

An axillary bud regulating composition for tobacco plants is provided, which contains a chlorobenzoylamino derivative of the formula

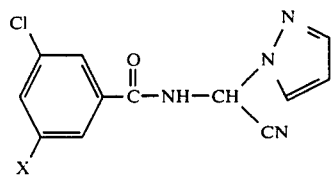

wherein X is a hydrogen or chlorine atom.

This composition is applied with a small concentration to tobacco plants. It does no harm to tobacco taste at all and has small persistency. It is able to control axillary buds grown as long as 4–5 cm and has enough rain-resistance.

6 Claims, No Drawings

TOBACCO AXILLARY BUD REGULATING COMPOSITION

This invention relates to a tobacco axillary bud regulating composition containing as the effective component of a chlorobenzoylamino derivative represented by the formula

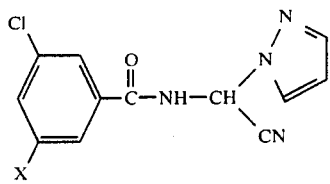

wherein X means a hydrogen or chlorine atom, namely 2-(3-chlorobenzoylamino)-2-(pyrazol-1-yl)acetonitrile (hereinafter referred to as the Compound [1]), or 2-(3,5-dichlorobenzoylamino)-2-(pyrazol-1-yl)acetonitrile (hereinafter referred to as the Compound [2]).

In cultivation of tobacco plants, the work to remove the axillary buds is indispensable. The removal of the axillary buds by hand is, however, a troublesome work, and needs a lot of labor.

Accordingly, the regulating method by use of a chemical agent is being taken up at present. Recently, maleic acid hydrazide has been most extensively used for this purpose.

Tobacco is a strongly tasteful article. It is important for the cultivation of tobacco plants to produce tobacco having improved quality, and of good taste, as well as to secure high yield.

The application concentration of maleic acid hydrazide, which is extensively used at present as the axillary bud regulating agent, is as high as about 5,000 ppm. It is one of problems that the taste of tobacco produced through removing the axillary buds with maleic acid hydrazide at such a concentration, is inferior to that of tobacco through hand removal of axillary buds. Therefore, appearance of an regulating axillary bud agent is desired, which is effective at a lower concentration and does not deteriorate the tobacco taste.

Another problem is the environmental contamination by certain agricultural chemicals. In this connection, the development of such an axillary bud regulating agent is looked for, which has small persistency and is effective even with a small amount application.

Under such circumstances, the present inventors have carried out the research work with the aim to develop such an outstanding axillary bud regulating agent which satisfies the above requirements. They have found that the compounds mentioned above have such significant regulating ability as is not surpassed by any of the conventional axillary bud regulating agents. Based on this new knowledge, this invention has been established.

The compounds according to this invention are already known to be the effective components for herbicides and fungicides (EP-76030A$_2$).

As stated above, the inventors have conducted the research work in order to develop such an outstanding tobacco axillary bud regulating agent as exceeds the maleic acid hydrazide which is widely used at present as the tobacco axillary bud regulating agent. Then, it has been confirmed that the necessity for such an agent is to satisfy the following three additional points.

(1) It is able to suppress the axillary bud formation at a lower concentration without deteriorating the tobacco quality.

(2) Even when the axillary buds grow up to length of 4–5 cm, the agent should be able to sufficiently control their growth.

(3) The agent should have enough resistance against rainfall after the application, and show the axillary bud regulating effect even when a rain continues.

The compounds employed in this invention also satisfy the above characteristic properties and are able to be applied as an outstanding tobacco axillary bud regulating agent which is superior to conventional maleic acid hydrazide. These facts have been found out by the present inventors for the first time as the result of their extensive investigations.

When the tobacco axillary bud regulating composition of this invention is applied in field, it may be blended with a solid carrier, a liquid carrier, a surface active agent, or other auxiliary agent for formulation, thus to prepare a wettable formulation, emulsion formulation or flowable formulation.

The examples of the solid carriers include fine powder or granules of kaolin, attapulgite, bentonite, acid clay, pyrophyllite, talc, diatomaceous earth, calcite, walnut powder, urea, ammonium sulfate, synthetic hydrous silica, etc.

As the liquid carriers, the followings are illustrated; aromatic hydrocarbon, such as xylene, methylnaphthalene, etc., alcohols, such as isopropanol, ethylene glycol, cellosolve, etc., ketones, such as acetone, cyclohexanone, isophorone, etc., and vegetable oils, such as soybean oil, cotton seed oil, etc., as well as dimethyl sulfoxide, acetonitrile, water, etc.

The surface active agents used for emulsification, dispersion, wetting, etc., include anionic surfactants, such as alkyl sulfate, alkyl or calcium dodecylbenzenesulfonate sulfonate, dialkyl sulfosuccinate, polyoxyethylene alkylaryl ether phosphoric acid ester salt, etc. as well as nonionic surfactants, such as polyoxyethylene alkyl ether, polyoxyethylene alkylaryl ether, polyoxyethylenepolyoxypropylene block copolymer, sorbitan fatty acid ester, polyoxyethylenesorbitan fatty acid ester, etc.

As the auxiliary agents for formulation, ligninsulfonate, ligninalginate, polyvinyl alcohol, gum arabic, CMC (carboxymethylcellose), PAP (isopropyl hydrogen phosphate), etc., may be employed.

The formulated agent may contain an effective component of this invention by 1–95%, preferably 5–80%, by weight.

The examples of the formulations are shown below. The part mentioned means the part by weight.

FORMULATION EXAMPLE 1

A mixture of 50 parts of the Compound [1], 3 parts of calcium ligninsulfonate, 2 parts of sodium lauryl sulfate and 45 parts of synthetic hydrous silica is well crushed and blended, thus to obtain a wettable powder.

FORMULATION EXAMPLE 2

Ten parts of the Compound [2], 14 parts of polyoxyethylene styrylphenyl ether, 6 parts of calcium dodecylbenzenesulfonate and 70 parts of xylene are mixed well, thus to obtain an emulsion formulation.

FORMULATION EXAMPLE 3

A mixture of 25 parts of the Compound [1], 3 parts of polyoxyethylenesorbitan monooleate, 3 parts of CMC and 69 parts of water is wet pulverized to obtain a flowable formulation in which particle size is 5 micron or less.

For the treatment of tobacco with the tobacco axillary bud regulating composition of this invention, the composition is diluted with water to make up a treatment concentration of normally from 300 to 3,000 ppm, and the diluted solution may be sprayed to, or coated, at the generating portions of axillary buds directly.

The tobacco axillary bud regulating composition of this invention can be combinedly used with another tobacco axillary bud regulating compound which is already known. Occasionally, such a combination may increase the tobacco axillary bud controlling efficacy, due to the synergistic effect.

These plant growth regulating compounds, which are already known and can be mixed with, include, but of course not limited to, higher alcohols, such as octanol, decanol, etc., maleic acid hydrazide and its salts, prime +(alpha, alpha, alpha, -trifluoro-2,6-dinitro-N-ethyl-N-2'-chloro-6'-fluorobenzyl-p-toluidine), butamifos i.e., 0-ethyl-O-(2-nitro-5-methylphenyl)-N-secondary-butyl phosphoramidothionate, trifluoromethanesulfonate anilide, and its salts.

Following examples show the axillary bud regulating effect of the tobacco axillary bud regulating composition of this invention. The axillary bud regulating effect is shown with the axillary bud regulating ratio as calculated by the following formula.

Axillary bud regulating ratio (%) =

$$1 - \frac{\text{Axillary bud fresh weight per tobacco stock with the chemical treatment}}{\text{Axillary bud fresh weight per tobacco stock without the chemical treatment}} \times 100$$

EXAMPLE 1

Tobacco Axillary Bud Regulating Test in a Greenhouse

By use of 1/2000 are Wagner Pots placed in a greenhouse, tobacco plants (variety: Matsukawa) were cultivated. When the plant height reached about 1 meter, just before the flowering, the plant is pinched at the top bud and used for the test. Each one tobacco plant was planted in one pot and each test was doubled.

An emulsifiable formulation of the Compounds produced according to the Formulation example 2 and a liquid formulation of maleic acid hydrazide choline salt sold in the market were diluted with water respectively to specified concentrations.

The diluted solution was sprayed to the stem and leaves in an amount of 20 ml per stock. The grown axillary buds on 30th day after the treatment were cut off and the whole fresh weight was measured. The average axillary bud fresh weight per stock was obtained and the axillary bud regulating ratio was calculated.

Table 1 shows the results.

TABLE 1

| Compounds tested | Treatment concentration (ppm) | Axillary bud regulating ratio (%) |
|---|---|---|
| Compound [1] | 1,000 | 100 |

TABLE 1-continued

| Compounds tested | Treatment concentration (ppm) | Axillary bud regulating ratio (%) |
|---|---|---|
|  | 500 | 100 |
| Compound [2] | 1,000 | 100 |
|  | 500 | 100 |
| Maleic acid hydrazide choline salt* | 2,500 | 31 |

*Control example

EXAMPLE 2

Tobacco Axillary Bud Regulating Test in a Field

Tobacco plants (variety: Matsukawa) were cultivated in a field. The plant was pinched at the top bud immediately before the flowering, and used for the test.

An emulsifiable formulation of the Compound [2] produced according to the Formulation example 2 and a liquid formulation of maleic acid hydrazide choline salt sold in the market were diluted with water respectively to specified concentrations. The diluted solution was sprayed to the stem and leaves in an amount of 20 ml per stock.

The lengths of the axillary buds before the treatment were 3-8 cm. Each treatment plot was planted with 3 stocks. On the 32nd day after the treatment, the grown axillary buds were cut off and the fresh weight was measured. The average axillary fresh weight per stock was obtained and the axillary bud regulating ratio was calculated.

Table 2 shows the obtained results.

TABLE 2

| Compounds tested | Treatment concentration (ppm) | Axillary bud regulating ratio (%) |
|---|---|---|
| Compound [2] | 2,000 | 100 |
|  | 1,000 | 100 |
|  | 500 | 98 |
| Maleic acid hydrazide choline salt* | 5,000 | 96 |
|  | 2,500 | 45 |

*Control example

APPLICATION EXAMPLE 3

Rainfall Resistance Test for the Tobacco Axillary Bud Regulating Efficacy

Tobacco plants (variety: Matsukawa) were cultivated in 1/2000 are Wagner pots placed in a greenhouse. The plants were pinched at the top bud immediately before the flowering and used for the test. One stock of tobacco was planted in one pot, and each test was trippled.

An emulsifiable formulation of the Compound [2] obtained according to the Formulation example 2 and a liquid formulation of maleic acid hydrazide choline salt were diluted with water respectively to specified concentrations. Each 20 ml of the diluted liquid was sprayed to the stem and leaves of the tobacco plant in an amount of 20 ml per stock.

Artificial rain was allowed to fall after lapse of 6 hours since the treatment was made. On the 30th day after the treatment, the grown axillary buds were cut off and the fresh weight was measured. The average axillary bud fresh weight per stock was obtained and the axillary bud regulating ratio was calculated.

Table 3 shows the results.

TABLE 3

| Compounds tested | Treatment concentration (ppm) | Artificial rainfall | Axillary bud regulating ratio (%) |
| --- | --- | --- | --- |
| Compound [2] | 1,000 | Yes | 100 |
| | 500 | Yes | 98 |
| | 1,000 | No | 100 |
| | 500 | No | 100 |
| Maleic acid hydrazide | 5,000 | Yes | 48 |
| | 2,500 | Yes | 10 |
| choline salt* | 5,000 | No | 97 |
| | 2,500 | No | 42 |

*Control example

EXAMPLE 4

Combination Test with Butamifos

Tobacco plants (variety: Matsukawa) were cultivated in a field. Immediately before the flowering, the top buds were pinched prior to the test.

An emulsifiable formulation of the Compound [2] obtained according to the Formulation example 2, and an emulsifiable formulation of butamifos were diluted with water respectively to specified concentrations. Each 20 ml per stock of the diluted solution was sprayed in single or combination to the stem and leaves. Each treatment plot was planted with 3 stocks.

On the 30th day after the treatment, the grown axillary buds were cut off and the total fresh weight was measured. The average axillary bud fresh weight per stock was obtained and the axillary bud regulating ratio was calculated.

Table 4 shows the results.

TABLE 4

| Treatment concentration | butamifos | | | |
| --- | --- | --- | --- | --- |
| | 1,000 ppm | 500 ppm | 250 ppm | 0 |
| Compound [2] 1,000 ppm | 100 | 100 | 100 | 100 |
| 500 ppm | 100 | 100 | 100 | 96 |
| 250 ppm | 100 | 100 | 100 | 72 |
| 0 | 84 | 71 | 25 | 0 |

We claim:

1. A method for regulating tobacco axillary bud which comprises applying to tobacco plants a tobacco axillary bud regulatory effective amount of a chlorobenzoylamino derivative of the following formula,

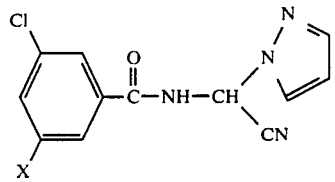

wherein X means a hydrogen or chlorine atom.

2. The method according to claim 1, in which the chlorobenzoylamino derivative is 2-(3,5-dichlorobenzoylamino)-2-(pyrazol-1-yl)acetonitrile.

3. The method according to claim 1, in which the chlorobenzoylamino derivative is 2-(3-chlorobenzoylamino)-2-(pyrazol-1-yl)acetonitrile.

4. A method according to claim 1 wherein the chlorobenzoylamino derivative is applied at a dosage of 300 to 3000 ppm.

5. A method according to claim 1 wherein the chlorobenzoylamino derivative is applied at a dosage of 500 to 1000 ppm.

6. A method according to claim 1 wherein the chlorobenzoylamino derivative is applied at a dosage of 500 ppm.